United States Patent [19]

Sparks et al.

[11] Patent Number: 4,675,140
[45] Date of Patent: Jun. 23, 1987

[54] METHOD FOR COATING PARTICLES OR LIQUID DROPLETS

[75] Inventors: Robert E. Sparks, Kirkwood; Norbert S. Mason, St. Louis, both of Mo.

[73] Assignee: Washington University Technology Associates, St. Louis, Mo.

[21] Appl. No.: 730,946

[22] Filed: May 6, 1985

Related U.S. Application Data

[63] Continuation-in-part of Ser. No. 611,583, May 18, 1984, abandoned.

[51] Int. Cl.[4] .............................................. B01J 13/02

[52] U.S. Cl. ...................................... 264/4.3; 264/4.4; 264/4.6; 264/4.7; 425/5; 427/213.33; 427/213.36; 427/240; 427/345; 424/450; 424/492

[58] Field of Search ................... 264/4.4, 4.6, 4.3, 4.7; 427/213.33, 213.36, 240; 425/5

[56] References Cited

U.S. PATENT DOCUMENTS

| | | | |
|---|---|---|---|
| 2,648,609 | 8/1953 | Wurster | 427/213 |
| 2,955,956 | 10/1960 | Baugh et al. | 427/215 |
| 3,015,128 | 1/1962 | Somerville, Jr. | 425/5 |
| 3,167,602 | 1/1965 | Bentov et al. | 264/4 |
| 3,415,758 | 12/1968 | Powell et al. | 427/213.33 |
| 3,672,932 | 6/1972 | D'Augustine | 427/240 X |
| 3,687,865 | 8/1972 | Katayama et al. | 264/4.3 X |
| 3,691,090 | 9/1972 | Kitajima et al. | 427/213.36 |
| 4,107,071 | 8/1978 | Bayless | 427/213.33 X |
| 4,187,194 | 2/1980 | Wellmann et al. | 427/213.36 |
| 4,218,409 | 8/1980 | Dannelly | 264/4 |
| 4,386,895 | 6/1983 | Sodickson | 425/5 |

FOREIGN PATENT DOCUMENTS

| | | | |
|---|---|---|---|
| 1090971 | 11/1967 | United Kingdom | 427/213.36 |

OTHER PUBLICATIONS

Kirk-Othmer Encyclopedia of Chemical Technology, Third ed., vol. 15, pp. 470–493 (1981).

"Spray Drying Handbook" by K. Masters, 3rd ed., John Wiley & Sons New York, pp. 179–184 (1979).

*Primary Examiner*—Richard D. Lovering
*Attorney, Agent, or Firm*—Holman & Stern

[57] ABSTRACT

Solid particles or viscous liquid droplets of core material are encapsulated in a coating material largely as single particles with a single coherent coating, by feeding a suspension of the two materials onto a rotating surface. The suspension is centrifugally dispersed by the rotating surface into relatively large coated particles and relatively small droplets of coating material. Only the size of the droplets of unused coating corresponds to the droplets formed from atomization of the liquid coating material. The size of the coated particles depends on the size of the uncoated particles and is much less dependent upon the atomization characteristics of the rotating surface. Upon being thrown from the rotating surface, or falling from that surface, the droplets and coated particles are solidified by exposure to air and are separated by sieving, or the like. The solidified droplets of pure coating material may be recycled into the suspension. Coating of all particles is achieved by dispersing the individual components of core material in the coating material before the resulting suspension reaches the rotating surface.

20 Claims, 15 Drawing Figures

U.S. Patent Jun. 23, 1987 Sheet 1 of 4 4,675,140

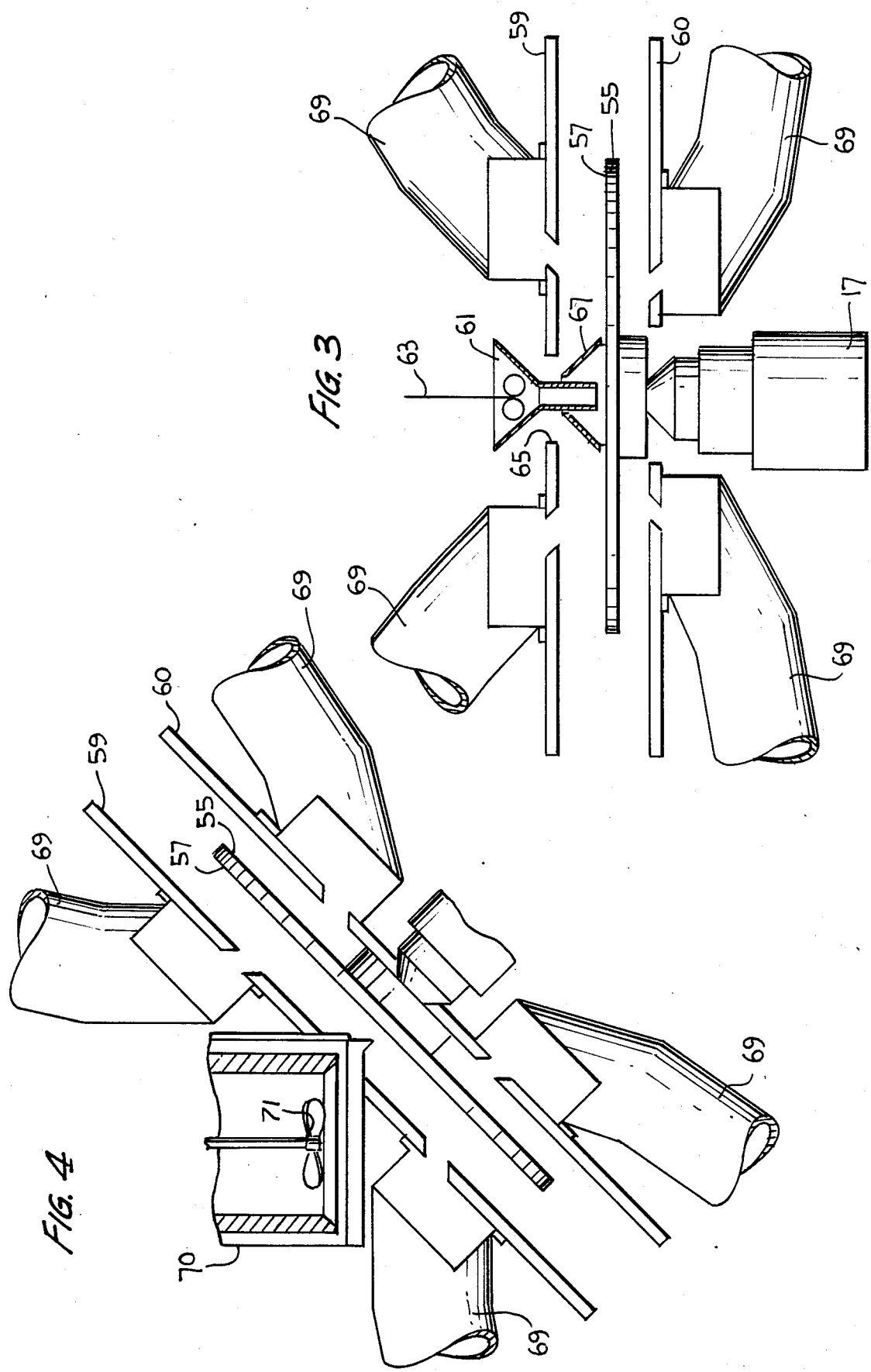

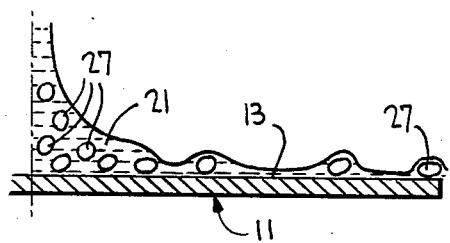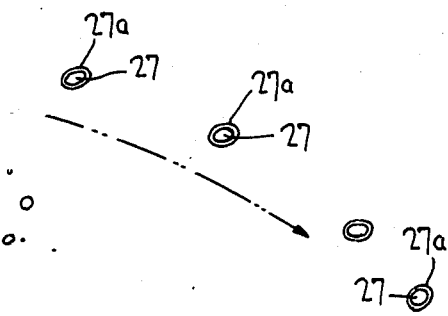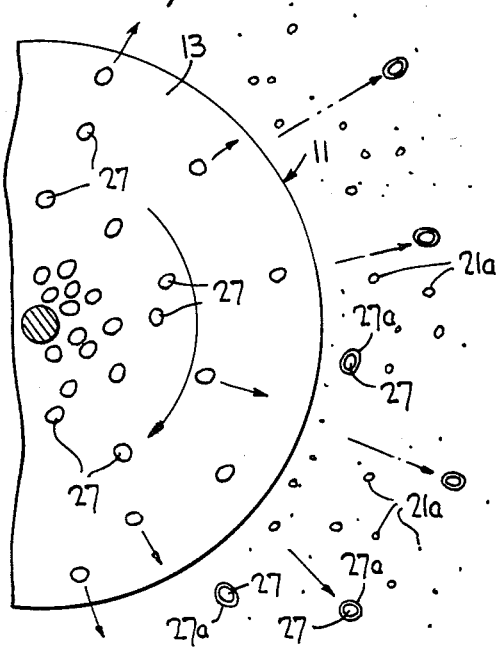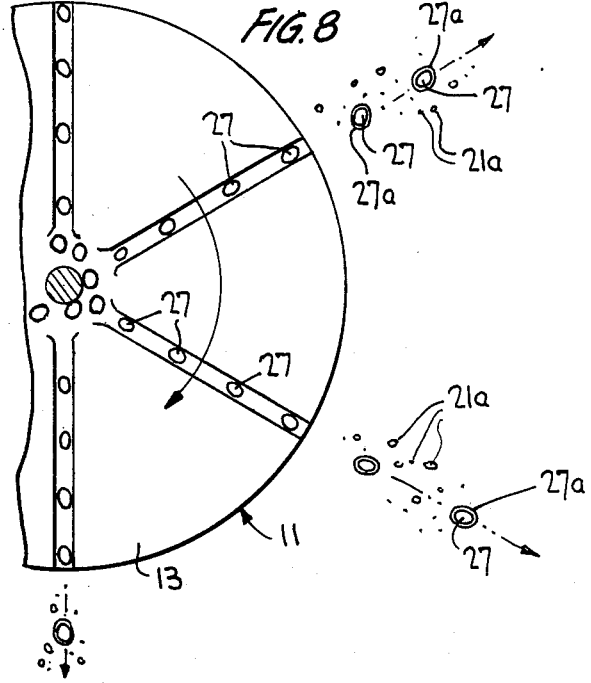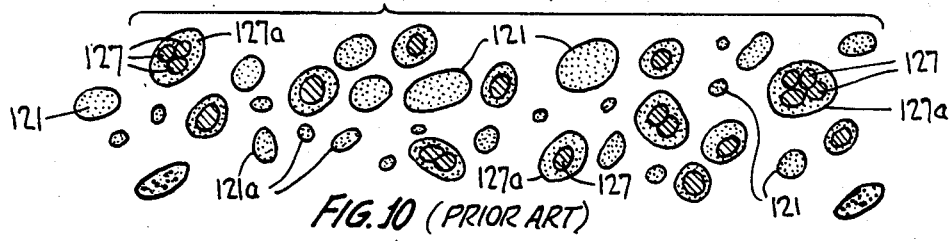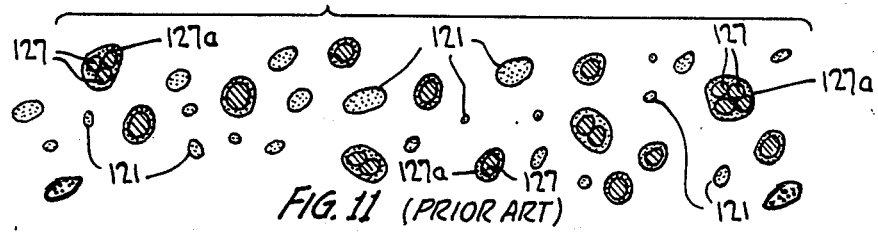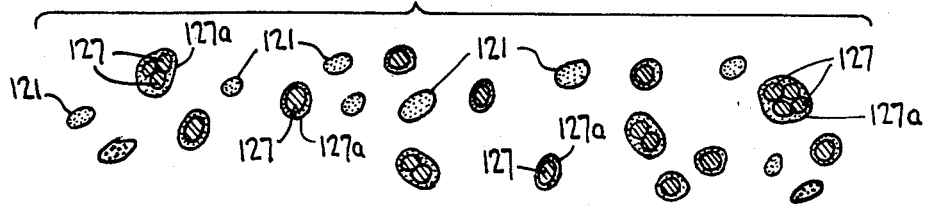

METHOD FOR COATING PARTICLES OR LIQUID DROPLETS

CROSS REFERENCE TO RELATED APPLICATION

This is a continuation-in-part of application Ser. No. 611,583, filed May 18, 1984 and now abandoned, for "Improved Method and Apparatus For Coating Particles Or Liquid Droplets". The entire disclosure of the parent application is expressly included herein by reference.

BACKGROUND OF THE INVENTION

1. Technical Field

The present invention relates to a method and apparatus for coating or microencapsulating solid particles or viscous liquid droplets. More particularly, the present invention relates to improvements in such methods and apparatus which provide encapsulation techniques and effects which are unprecedented in the prior art.

2. Discussion of the Prior Art

Coating or microencapsulation of solid particles or liquid droplets is widely employed to protect coated substances from environmental effects and/or control their release time and/or confer improved handling characteristics. Typical products which are coated or microencapsulated are drugs, pesticides, dyes, etc..

Numerous coating or microencapsulation techniques have been employed in the prior art, many of which are described in the Encyclopedia Of Chemical Technology, third edition, volume 15, pages 470-493 (1981), John Wiley and Sons. By and large, these techniques suffer from one or more important disadvantages, including: high cost; inapplicability for coating particles smaller than 200 micrometers in diameter; complexity; long contact time between the core and coating materials prior to solidification of the coating material; inability to achieve wetting and coating of the core particles with the desired coating material; inefficient separation of coated particles from unused coating material and inefficient usage or wastage of coating material. Also important in many methods are the tendency for the coated particles to agglomerate and the limited choice of wall materials. There are severe cost disadvantages to most methods because they are batch processes difficult to operate on large commerical scale and because they must employ a solvent for the coating and are unable to use melted coating materials, which require no solvent removal or handling facilities.

There have been a number of attempts in the prior art to provide coating techniques which are devoid of the aforesaid disadvantages. For example, in U.S. Pat. No. 4,386,895 (Sodickson), there is disclosed a rotating apparatus having radially-extending conduits from which hollow needles project radially outward into a reservoir of jelling material. As the apparatus spins, liquid core material is urged by centrifugal force through the conduits and needles. The liquid core material is formed into droplets at the distal ends of the needles, and the droplets are centrifugally thrown into a layer of the gelling material which forms on the outer reservoir wall due to the centrifugal forces produced by rotation. The droplets of liquid core material are thusly encapsulated by the gelling material. This technique works well for its intended purpose. However, it is limited to use with liquid as a core material (i.e., it cannot be used to microencapsulate solid particles) and the minimum size droplet that can be coated depends upon the inner diameter of the needle. As to the latter limitation, there are practical limitations on minimum needle size, particularly when viscous core liquids must flow therethrough.

In U.S Pat. No. 2,955,956 (Baugh et al.), a rotating disc or table is disposed below a feed pipe through which a slurry composition of coating material is fed. The slurry is spread over the spinning disc surface to form a thin film of the coating material thereon. An annular flow of solid granules is permitted to impinge upon the film on the disc surface, whereupon the granules are coated with the coating material. The coated granules are thrown or are permitted to fall from the rotating disc and are solidified by dry warm gas directed at the falling granules. A second annular flow of granules is directed onto the rotating film to scavenge the unused film and assure that all of it is utilized. Again, this technique is satisfactory for a limited purpose, namely coating granules, such as salt, with additives, but it cannot be readily employed to coat liquid droplets. Moreover, since the granules in the scavenging outermost annular flow cannot possibly be coated to the same extent as granules in the innermost flow, it is not possible with this technique to achieve uniform coating of all of the granules. Therefore, the Baugh et al. technique is more suitable for wide dispersion of additives onto the surface of granules than it is for coating particles.

British Pat. No. 1,090,971 to Wilson, et al., discloses a method of microencapsulating solid particles by forming a dilute suspension of the particles in a dilute solution of a resinous coating material in a volatile liquid, causing the suspension to impinge on a spinning disc whereby the dilute suspension is dispersed as a spray consisting of atomized coating solution and microencapsulated particle droplets, the spray of droplets then being exposed to steam at temperatures above the boiling point of the coating solvent which volatilizes the unwanted liquid solvent so as to leave coated particles plus particles of pure coating of the same size. The process, however, requires a feedstock solution having a very low percentage content of particles to be coated, involves the high temperature removal of a large amount of unused feedstock liquid by volatilization, and does not permit separation by sizing of coated particles from particles of pure coating material.

OBJECTS AND SUMMARY OF THE INVENTION

It is therefore an object of the present invention to provide an improved method and apparatus for coating or microencapsulating both solid particles and viscous liquid droplets.

It is another object of the invention to provide a method and apparatus for microencapsulating particles which enables at least a majority of the particles to be coated individually or discretely rather than in clusters while simultaneously providing improved means for separating unwanted and unused liquid coating material from the coated particles. More particularly, it is an object of the invention to provide a coating process and apparatus which includes controlled mechanical or physical separation of coated particles from unused liquid coating material by size discrimination whereby the method is equally applicable to the coating of solid or viscous liquid particles, either with materials including a liquid solvent or with molten coating liquids, and whereby the wettability of the core particles or droplets by the coating material is relatively unimportant, permitting use of the method for a wider variety of core particles and coating materials.

It is another object of the present invention to provide a method and apparatus for coating or microencapsulating solid particles and viscous liquid droplets over a wide range of particle and droplet sizes, including droplets and particles having diameters well below 200 micrometers.

It is a further object of the present invention to provide a method and apparatus for coating or microencapsulating solid particles or viscous liquid droplets with much less complexity, continuously, at a much faster rate, and at lower cost than is possible in much of the prior art, and to avoid the problem of agglomeration of the particles being coated.

Still another object of the present invention is to provide a method and apparatus for coating or microencapsulating solid particles or viscous liquid droplets wherein coating material can be easily re-cycled back into the process if not used during a first pass through the process.

It is yet another object of the present invention to provide a method and apparatus for coating or microencapsulating solid particles or viscous liquid droplets in which coating thickness can be easily adjusted by adjustment of any of plural process parameters.

A further object of the present invention is to provide a method and apparatus for coating or microencapsulating solid particles or viscous liquid droplets wherein the contact time between the core and coating materials prior to solidification of the coating material can be made sufficiently short to prevent degradation of some labile materials, or to prevent their dissolving one in the other when they are partially or totally miscible.

The present invention provides, in a process for coating particles with a liquid coating, a method for obtaining individually coated particles while simultaneously facilitating removal of the coated particles from excess coating liquid with which the particles are mixed in a suspension, the method comprising feeding the suspension onto a rotating surface to separate the suspension into coated particles and atomized liquid droplets expelled circumferentially from the surface, and rotating the surface at a speed yielding a predominance of the droplets of undesired liquid coating of a predetermined size which is smaller than the size of the coated particles.

Thus in accordance with the present invention, solid particles or liquid droplets of core material to be coated are initially dispersed in molten or dissolved coating material to form a suspension. The suspension of the two materials is then fed to the surface of a rotating disc, table or other rotating element. The process parameters, particularly the speed of rotation of the disc or other rotating element are controlled so that the centrifugal forces imposed on the suspension by the disc or the like cause the suspension to spread towards the disc periphery with progressive thinning out of the liquid and separation of excess coating material from the coated particles, with dispersion of the suspension into (1) large coated particles and (2) significantly smaller-size atomized droplets of excess coating material which are formed by atomization of the thin film of liquid coating at the periphery of the disc or the like. Thus, in accordance with the invention, the disc or the like is used as a means for mechanically or physically separating the excess coating liquid from the individually coated particles and dispersing the separated liquid as atomized droplets of significantly smaller size than the coated particles. Most importantly, to obtain the required separation and dispersion, the invention involves relating the rotary speed of the disc to the required size of atomized droplets of excess liquid coating material to be obtained from the disc, rather than relating the disc speed to the size of coated particles to be obtained. This represents a significant departure from known techniques involving the use of a rotating wheel or the like to provide dispersion of coated particles, where the wheel speed is related to the required size of coated particle products. In practical terms, for coated particles of comparable dimensions, the invention involves rotary disc speeds surprisingly in excess of those used in the prior art techniques.

The average mean size required for the atomized droplets of excess coating liquid may, in practice, be determined by the amount of contamination, i.e., excess unused coating material, which is acceptable in the final product of coated particles, such determination being effected by known techniques involving the relative sizes of the coated particles and the particle size distribution characteristics of unused coating liquid, related to rotational speeds, liquid feed rate, length of wetted periphery, and viscosity in rotary atomizer-type equipment. Typically, in accordance with the invention, the average size of atomized droplets may be about 20% to 75% of the size of the coated particles.

Since the materials being coated are solid (or viscous liquid), they are not atomized but are simply thrown from the disc as relatively large particles retaining a coating of the liquid in which they were immersed. The control of the process parameters to provide separation of the suspension by the rotary disc into individually coated particles and significantly smaller droplets of excess coating material differentiates the process of the present invention completely from prior art processes such as spray congealing, in which a slurry of dispersed solids is atomized as a liquid, with the product solid present inside the atomized droplets. In spray congealing the dispersed solids are sufficiently finely divided that there are many solid particles in most of the atomized slurry product, and the size distribution of the entire product approximates that predicted from atomization correlations. In spray congealing, when the suspension must behave as a liquid during atomization and no solvent is subsequently removed, the volume fraction of solids in the suspension (and hence, also in the product congealed droplets) has an upper limit near 30%, while in the present invention the volume fraction of coated solids in the product particles may be in excess of 90%, owing to the separation of the unused coating liquid on the rotating disc and its atomization into smaller, easily removed particles. In the present invention essentially all of the solids in the feed slurry and all of the coated product solids are larger than the sizes predicted from atomization correlations for the processing conditions employed. An example of the size distribution of the feed solids, product solids and atomized coating obtained is provided in Example VII.

The invention further has clear distinctions from the old art of spray-chilling, in which a suspension is atomized with subsequent solidification of the droplets by cooling, and from spray-drying, in which a solvent is present in the original suspension or solution and is subsequently removed. In both these known processes, the feed suspension or solution is atomized as a liquid, and the products of the processes are the solidified droplets, and there is no separation between particles containing solids and those not containing solids. In principle any atomization device can be used which will give the desired droplets. In the present invention, the process variables are adjusted to give a completely different result, and products can be formed which are impossible to form in general spray-chilling or spray-drying. For example, it is convenient with the process invention to place thin waxy coatings (e.g. 100 micrometers) around solid particles 2 millimeters in diameter. In spray-chilling, it would not be possible to pass the feed slurry through a pressure nozzle or two-fluid nozzle, because the core particles would block or plug the orifices in typical nozzles. If a very large nozzle was used to permit the particles to pass, the resultant coarse spray would include many product particles containing no core (just large drops of coating), a few core particles having thin coating, many having thick coating and many in agglomerates rather than as single coated particles. This would occur because particle formation in these orifice devices occurs by atomization of the entire slurry simply as a liquid which happens to contain some solid particles. Such a slurry of large particles could, of course, be passed over a rotating-disc atomizer without any plugging or flow stoppage. However, the disc would be run to treat the slurry as a simple fluid, giving all atomized droplets in the same size range. Again, this means that much of the coating would be in the form of particles as large as the coated particles and many of the particles will be in the form of agglomerates. In none of these cases could most of the unused coating be separated from the coated particles by simple means such as sieving, and the product would contain large inert particles of coating as a major fraction. This is unacceptable in most practical cases.

By contrast, in the present invention, with a feed slurry containing e.g. 500 micron core particles, and a desired coated product particle of 600 micron average diameter, the disc size, rotational speed, feed rate of the slurry and coating viscosity will be adjusted to force all the unused coating to be in the form of droplets much smaller (e.g. a mean diameter around 250 micrometers) so that most of it can be easily separated from the product, and the product particles will essentially be all in the form of single coated core particles nearly all having an average coating thickness of 50 microns. If it is desired, it is possible to make the unused coating particles smaller, or somewhat larger, while making the desired product.

A key point of the invention is to run the process differently from a typical spray-chilling process. In the latter process, the atomization is set to treat all the feed slurry as a liquid, making droplets in the desired size range. In the process invention, all parameters are adjusted to force all unused particles into a relatively small size, formed by atomization of the film of pure coating, while the large product of coated core particles is thrown off the disc surrounded by the desired amount of remaining liquid, subsequently solidified as a coating.

The small coating material droplets and the coating-wetted particles resulting from operating the disc in accordance with the invention are thrown or caused to fall from the spinning surface and solidify due to the drying or cooling effect of the surrounding air or gas. Sieving or other size discrimination techniques may be readily employed to remove the coated particles from the much smaller particles of unused coating material and the removal step is facilitated compared with prior art processes because of the size discrimination between the coated particles and the smaller particles of excess coating material which is conferred by the process invention. The coating material particles thusly collected may be re-cycled into the process. The minimum size of the solid particles or liquid droplets which can be coated by this technique is limited only by the size of the particles or droplets themselves and by the lower limit of droplet size of excess coating liquid which can be obtained with a rotating disc (dry particles of 1–5 micrometers at high disc speeds with low viscosity coatings containing solvent). By completely dispersing the particles or droplets in the molten coating material before the materials are placed in contact with the rotating surface, it is possible to coat all particles in a similar fashion. The more uniform the size of the dispersed particles the more particle-to-particle uniformity there will be in the coated particles. This has little effect on the size distribution of smaller, atomized excess coating.

BRIEF DESCRIPTION OF THE DRAWINGS

These and other objects, features and many of the attendant advantages of the present invention will be better understood upon a reading of the following detailed description considered in connection with the accompanying drawings wherein like parts in each of the several figures are identified by the same reference numerals, and wherein:

FIG. 3 is a diagrammatic representation of still another embodiment according to the present invention;

FIG. 4 is a diagrammatic representation of a further embodiment employed in accordance with the present invention;

FIG. 6 is a diagrammatic elevational view of a rotary separating element showing its effect on a liquid suspension when used in accordance with the invention;

FIG. 7 is a diagrammatic plan view of the element shown in FIG. 6;

FIG. 8 is a view similar to FIG. 7 but showing another type of rotary separating element;

FIGS. 9, 10 and 11 are diagrammatic views of prior art products (from a spray drying process) including coated particles, the figures representing successive stages in a coating process;

DESCRIPTION OF THE PREFERRED EMBODIMENTS

Figure 1:
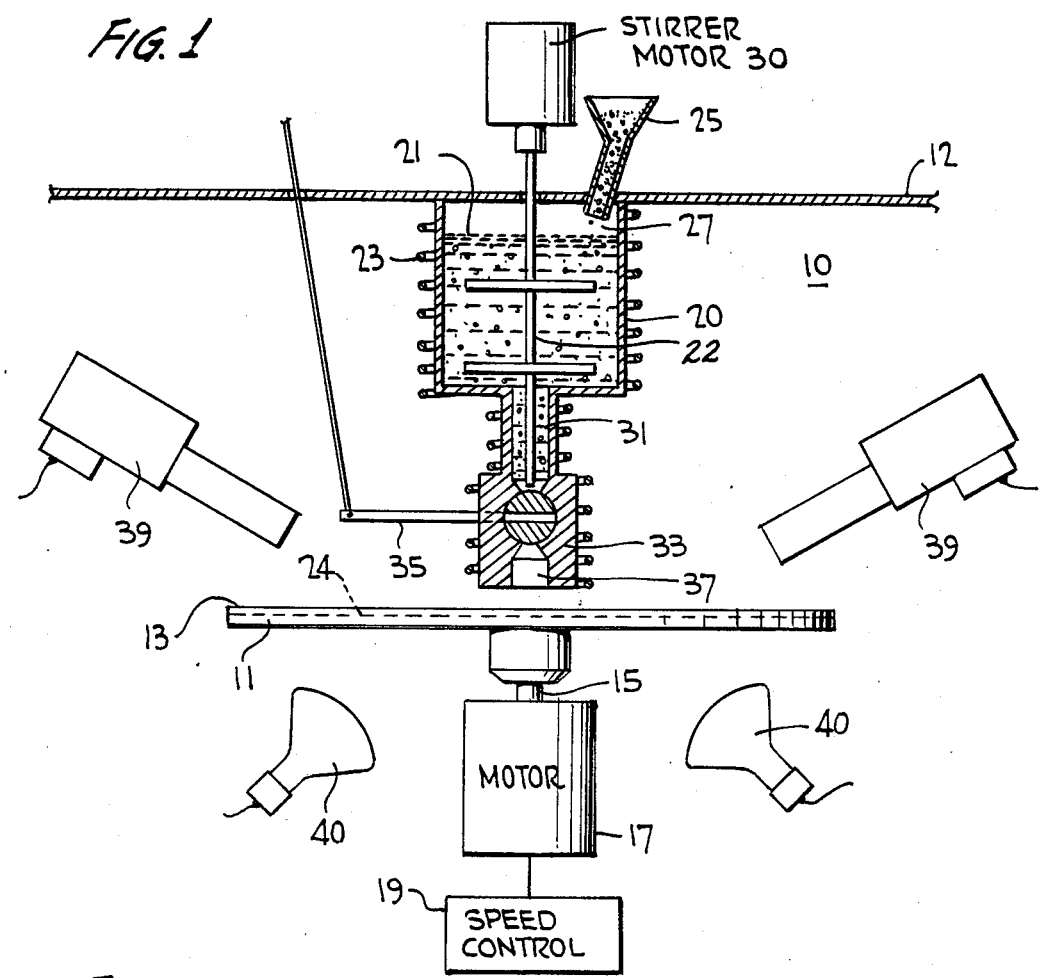
FIG. 1 is a diagrammatic illustration of apparatus according to the present invention which may be employed to perform the method of the present invention.

Referring specifically to FIG. 1 of the accompanying drawings, an enclosed spray chamber 10 (with only top wall 12 illustrated in FIG. 1) is provided for performing the method of the present invention. Within chamber 10 there is disposed a rotatable disc or table 11 having an upper surface 13 which may be disposed horizontally. Rotatable disc 11 is rotatably driven about its central vertical axis by means of a variable speed drive motor 17 acting through drive shaft 15. A speed control unit 19 permits adjustment of the rotational speed of the disc 11.

Speed control 19 and motor 17 may be located inside or outside of chamber 10, depending upon the particular application. The disc may be disposed above the motor or suspended below the motor, with appropriate modification of feed lines, supports, etc.

A reservoir 20 is adapted to contain molten or dissolved coating material 21. The reservoir 20 is heated, for example, by means of a heating coil 23 disposed about the reservoir periphery, to maintain the coating material 21 in molten or dissolved form. In this regard, the coating material 21 may be supplied to reservoir 20 in molten form and maintained in that state by means of the heating coil; alternatively, the coating material may be supplied to the reservoir in solid form and melted by the heat derived from heating coil 23. In either case, the molten coating material 21 in the reservoir is in a flowable state. A feed funnel 25 is provided to extend through an opening in chamber 10 so as to deliver individual mass components 27 of core material (e.g., solid particles of core material) to be coated into reservoir 20. In instances where the core material is in the form of droplets of viscous liquid, funnel 25 may be replaced by a droplet-forming tube, a means of feeding an emulsion or the like. A stirrer mechanism extends into the chamber 10 and reservoir 20 and is actuated by a variable speed stirrer motor 30 disposed outside of chamber 20. The stirrer 22, when driven by motor 30, acts to disperse the solid particles 27 (or liquid droplets) of core material throughout the molten coating material 21. The result is a slurry or suspension of the two materials disposed in reservoir 20. This slurry or suspension is delivered through a gravity-feed passage 31, extending from the bottom of reservoir 20, to a ball valve mechanism 33. The ball valve 33 is selectively actuatable from outside chamber 10 by means of actuating rod 35 to control the rate of flow of the suspension material through the ball valve 33. It is noted that the heating coil 23 is disposed so as to heat the suspension as it passes through passage 31 and ball valve 33, thereby assuring that the coating material remains in its molten state while in these components. The outlet passage 37 from ball valve 33 is disposed directly above the axial center of surface 13 so as to deliver the suspension material substantially along the rotation axis of disc 11.

The space above surface 13 is heated, for example, by means of industrial grade heat guns 39, to maintain the temperature on surface 13 sufficiently high so that the coating material in the suspension remains molten. Additional heat is provided at the underside of disc 11, for example, by means of infrared heat lamps 40. Heating may be provided by many methods such as preheated air, steam, radiant energy, induction heating, etc.

The top surface 13 of disc 11 may be smooth or may be provided with a plurality of angularly-spaced radially-extending grooves 24 defined therein, or raised fins, so as to establish paths of travel for the material deposited on surface 13 from ball valve 33. Grooved or vaned surfaces are advantageous if the particles to be coated are small, for example below 200 micometers in diameter, and the coating is viscous, because they can produce finer particles of the unused liquid coating than do smooth discs at the same rotational speed.

In operation, the coating material 21 in liquid or slurry form is disposed in reservoir 20. If the coating material 21 is a wax, the wax is melted by heating. If a polymer coating material is used, it may be dissolved in a solvent, if necessary. The coating liquid may contain emulsified or suspended particles if they are desired in the final wall or coating on the core particle. The core material must be solid particles, granulated aggregates of fine particles or droplets of liquid which is more viscous than the liquid coating material 21. These particles or droplets 27 preferably, but not necessarily, should have a relatively narrow size distribution. When the droplets or particles are fed into the slurry of coating material 21, the stirrer 22 may be actuated by stirrer motor 30 to disperse the particles 27 in the material 21. With the particles properly dispersed (and this may be a continuous process), the disc drive motor 17 is actuated and set to the desired speed by speed control 19. This desired speed will depend primarily upon the size of the smaller excess coating particles to be produced as described below. Ball valve 33 is then actuated by means of actuator rod 35 to permit the suspension to flow onto the surface 13 of disc 11. Valve 33 is opened slowly until the desired flow rate is achieved. The centrifugal force acting upon the suspension material as it hits the surface 13 causes the material to be thrown radially outward on the surface or grooves 24. This has the effect of dispersing the suspension into both particles 27 wetted with the coating liquid and smaller droplets of coating liquid which do not contain the core particles 27. The heating of the region surrounding disc 11 maintains the coating material in liquid state on surface 13. However, when the material is thrown from or falls from disc 11, the material falls through dry cooler air which causes the coating material to solidify by cooling or drying. The solidified small droplets of excess coating material and the core material coated with the solidified coating material fall to the bottom of the chamber during the solidification process. Sieving, or other separation techniques, may be employed to separate the coated particles from the smaller particles of pure coating material. The smaller coating material pieces may then be recycled into the process by delivering such pieces into reservoir 20. The majority of the original suspended particles are coated discretely and similarly, a feature which is achieved by virtue of the fact that the original core material particles 27 are carefully dispersed in the coating material before the suspension is fed to the rotating disc. The coating thickness may be varied mainly by changing the viscosity of the coating liquid, but also by adjusting the feed rate of suspension to the disc, by varying the rotational speed of the disc, by varying the diameter of the disc or by varying the number of grooves or vanes.

It is possible to perform the method of the invention as a continuous process by feeding the coating liquid 21 and particles 27 into reservoir 20 on a continuous basis. An endless conveyor belt disposed at the floor of chamber 10 collects the particles and feeds them to a train of sieves which discriminate between coated particles and the smaller particles of pure coating material. The latter may be delivered directly to the reservoir 20 whereas the coated particles may be dispensed in any manner desired. Alternatively, all of the particles may be pneumatically conveyed into a cyclone, seives or bag filter for separation of smaller excess coating droplets to be recycled.

As previously noted, the process parameters are specifically controlled, in a manner to be described, so as to provide a separation of the liquid suspension by means of the disc into coated particles (generally these will be individually coated particles unless the process is operated at low enough speed so that a small fraction of the particles remain as doublets or triplets, or if there is a wide size distribution of feed particles such that the finer core particles are trapped in larger particles) and droplets of excess coating liquid of significantly smaller size than the coated particles. The effect of the rotating disc on the suspension fed to it is vividly illustrated in FIGS. 6 to 8. It will be seen that the coating liquid 21 in the suspension is gradually pulled away from the core particles 27, forming a liquid film on the disc, as the suspension moves from the center toward the periphery of the disc, with progressive decrease in thickness of the liquid film or sheet and finally separation of the excess liquid from the particles 27, leaving a coating layer 27a on the particles and dispersing the excess coating into a spray of small droplets 21a formed from the thin coating film. FIGS. 6 and 7 show this effect for a disc with a smooth upper surface, and FIG. 8 shows the effect with a grooved disc. The size of the atomized droplets of excess coating bears little relation to the size of the solid coated particles, but depends rather on the film spreading and atomization characteristics of the liquid coating alone. The core particles, by contrast, move by a totally different mechanism, not spreading into a film but simply being thrown through or along the film of coating, issuing from the disc periphery with a small amount of associated coating material.

Figure 12:
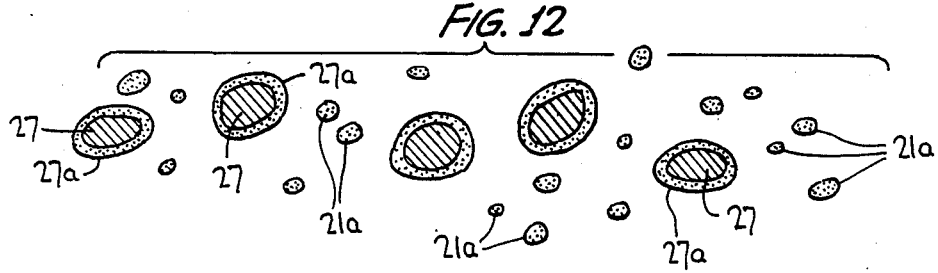
FIG. 12 is a view similar to FIG. 9 showing an intermediate product according to the invention prior to final separation of coated particles from droplets of excess coating liquid.

FIG. 12 shows a typical product in accordance with the invention as it is sprayed or expelled from a rotating surface. It will be evident that the product consists of core particles 27 with a liquid coating layer 27a all generally of similar size, and droplets 21a of excess unused coating material 21 which are of significantly smaller size than the coated particles and which have a size distribution typical of that expected for simple atomization of the pure coating liquid. The product shown in FIG. 12 is in vivid contrast to typical products of prior art processes which use a rotary wheel or the like to provide dispersion of suspended particles. Thus, FIGS. 9 to 11 show the product of a typical prior art process (spray drying) in which particles are imbedded in droplets of a liquid containing a solvent, by forming a slurry of the particles in the liquid and forming droplets of the slurry by feeding the slurry to a rotary wheel or the like. As shown in FIG. 9, the product as it leaves the wheel contains particles 127 with a liquid coating 127a and separated droplets 121 of excess coating material. However, it will be evident that there is no sharp size discrimination, as in products of the present invention, between the coated particles (which are usually coated in clusters, but some of which will be coated singly) and the droplets of excess coating material. Thus, there are a significant number of droplets 121 which are comparable in size to the coated particles, in contrast to products of the present invention where the droplets predominantly are significantly smaller than the coated particles and most large particles are coated discretely. Accordingly, subsequent removal of excess droplets of coating material, by sieving, centrifuging or the like, is facilitated with products according to the invention compared with the products of the prior art processes. FIG. 10 shows the prior art product of FIG. 9 after evaporation of the solvent, and FIG. 11 shows the product after removal of the smaller excess coating droplets, for example by sieving, illustrating the rather high percentage of unused coating material (in the larger droplets thereof) which has not been removed from the coated product. It is essentially impossible by this prior art process to produce product particles with core loadings above 50%, to remove excess coating, and to have high particle-to-particle uniformity.

Looked at in the alternative, the invention provides a product comprising relatively large, predominantly individually coated particles and uncoated droplets predominantly of significantly smaller size than the coated particles, whereas prior art products are predominantly a mixture of individual mass components of coated particles and uncoated droplets of generally similar dimensions wherein the core particles themselves are relatively small compared to the final particles.

In order to obtain a product wherein there is a sharp size discrimination between the coated particles and the droplets of excess coating liquid, the process parameters in accordance with the invention are controlled in a particular manner. More particularly, in accordance with the invention, the rotational speed of the disc or the like is related to the average mean size required for the droplets 21a (as will be described in more detail below) rather than relating the rotational speed of the disc or the like to the average size required for the coated particles. By contrast, in the prior art processes, the speed of the rotary wheel or the like is related to the size required for the formed droplets irrespective of whether they contain imbedded core particles or not. Thus, in the present invention, the disc or the like is run at surprisingly higher speeds than in the prior art for producing coated core particles of similar size to the particles of the prior art.

As noted above, in carrying out the invention, the speed of rotation for the disc is related to the required mean droplet size for the excess coating material rather than to the required size of coated particles and in this process, changes in the disc speed have significantly less effect on the thickness of coating on the large core particles. It is well known in industrial spray drying and spray chilling techniques using rotary disc-type atomizers that there are mathematical correlations between the disc speed and the average droplet size expelled from the disc, see for example pages 179–184 of "Spray Drying Handbook" by K. Masters, 3rd Edition, John Wiley & Sons, New York (1979), and which is specific incorporated herein by reference. These correlations may be used to provide an estimate of required disc speed for the present invention, (possibly incorporating a viscosity correction factor in the correlations to compensate for the effect of hot air flow as in FIGS. 3 and 4) once the desired average droplet size for the excess coating liquid has been established. This desired average droplet size may be established from known droplet size distribution estimates, for example, using log-probability graphs (also discussed in the above reference) and relating the estimated droplet size distribution to the acceptable contamination percentage in the final product, i.e., the percentage of acceptable excess coating droplets of a size making them impractical to separate from the coated particles. Again, it should be stressed that while techniques are known for estimating disc speed in relation to a required droplet size and for estimating droplet size distributions, these have not previously been utilized in the present manner whereby, in a particle coating process, disc speed is related to a predetermined size required for the droplets of excess coating liquid rather than being related to the size required for the coated product particles themselves. Also, it is understood that the correlations referred to above for determining the required disc speed may be used for estimation purposes, and in practice, it may be desirable somewhat to adjust the disc speed empirically.

To illustrate the significant difference in rotational speeds used in processes according to the invention compared with prior art processes, the various parameters used in a typical prior art spray cooling-type particle embedding process may be compared with the parameters used in a process in accordance with the invention for coating like particles with a like liquid coating. Thus, for example, if it is required to coat ion-exchange resin beads having a sieve fraction 53–106 microns with a wall material of 9/1 paraffin wax/Elvax 420 (Dupont ethylene-vinyl acetate copolymer, melt index 150), in a spray cooling procedure in accordance with a typical prior art process, the rotational speed of an 8-inch diameter (0.2 meter) disc type atomizer typically would be set at about 3,000 r.p.m. for a feed rate of 4.5 kg/hr of slurry containing 2/1 wt ratio of coating to core particles, with a coating viscosity of 50 centipoise to give an average fluid drop in the atomized slurry close to the size just containing the largest core particle. For the largest single core particle at 70% loading in the final microcapsule, this droplet size would be 120 microns and setting the rotational speed at 3,000 r.p.m. would give an average droplet size of about 118 microns from the correlation noted above. However, this will be the average particle size in the atomized slurry both for particles containing the core material and also for droplets of the excess pure coating material. A product obtained from this prior art process at these conditions showed a substantial overlap in particle size distribution of the coated particles and the unused coating droplets so that it was not practical to effect a separation based on size.

By contrast, in a process in accordance with the present invention, if it is estimated that the smallest microencapsulated product including the above beads will have a diameter of 67 microns at approximately 50% loading of the 53-micron core particle, the rotational speed of a disc may be set for example to run at 8,000 r.p.m. to give an average particle diameter for unused coating droplets of about 40 microns. To estimate the amount of unused coating droplets which might be in the microencapsulated product, a log-probability graph, as described above may be used and results in a contamination rate of about 10% for a product sieved at 67 microns. A run was also made under these conditions, but using an 8-inch vaned disc giving somewhat smaller droplets of excess coating. After sieving at 53 microns, the contamination, measured by counting coated particles and remaining pure coating particles, was approximately 7%.

The correlation referred to above with the viscosity term modified to mirror the effect of hot air moving over the surface is:

$$\bar{x} = \frac{(1.4 \times 10^4)(M_L)^{0.24}}{(Nd)^{0.83}(\pi d)^{0.12}} \left(\frac{V}{15}\right)^{0.1}$$

where $\bar{x}$ = Average droplet diameter (microns)
$M_L$ = Liquid feed rate (kg/hr)
$N$ = Rotational speed (RPM)
$d$ = Disk diameter (meters)
$V$ = Viscosity (centipoise)
$\pi d$ = Wetted periphery (meters). Use nh for disks with n vanes or grooves h meters high.

As noted above, one of the parameters which may be adjusted to vary the thickness of the coating material on the final coated particle is the viscosity of the coating liquid. In this regard, when wax is employed as a coating material, the viscosity can be readily lowered to thereby provide thinner coating walls on the final coated particle, by adding solvents to the molten coating material 21. When the inclusion of a polymeric material, e.g., polyethylene in the coating is desirable the viscosity can be lowered significantly through addition of compatible materials of substantially lower viscosity, e.g., waxes. In general, the solid particles 27 of core material should be insoluble in the liquid coating material 21; however, if the contact time between the core material 27 and the coating material 21 is sufficiently short before the coating material solidifies, solids may be coated before they dissolve. In this way, water soluble or water sensitive solids may be coated by an aqueous solution. Likewise, droplets of viscous liquids (i.e., of significantly greater viscosity than the coating material 21) may also be coated.

In some applications the materials may be selected such that the solid core material 27 reacts with the coating liquid 21 so as to form an initial solid wall at their juncture before the coating material 21 is solidified during the process. Thus, the core material 27 might contain a polyfunctional acid chloride, or isocyanate, and the liquid 21 might contain a polyamine or polyol. This technique is also useful for coating a liquid since the initial wall or shell formed by the chemical reaction between the two materials prevents absorption or dispersal of the core material into the coating material or aggregation of the core particles before the coating material solidifies.

Coatings of slurries may be formulated by suspending the solids desired in the coating liquid prior to, or simultaneously with, the suspension of the core particles. Suspended solids in the coating may be soluble in the coating if their contact time with the coating is insufficient to permit dissolution.

Liquids may also be coated by dispersing them to form a suspension or emulsion in the coating liquid. The core liquid should have a viscosity higher than that of the coating liquid so that the spread of liquid and subsequent atomization into small drops occurs primarily in the coating liquid. Liquid core materials may also be coated after they are absorbed onto or into solids.

It is also possible to catch the coated particles on a layer of powder or in a hardening or extraction bath in which additional solvent is removed by extraction or in which a chemical hardening reaction occurs. An example of the latter would be the formation of gelatin-coated particles which are caught in a bath containing glutaraldehyde which hardens the wall or coating material and greatly decreases the permeability of the wall.

It is possible to use the invention to produce walls of polymers which are insoluble in all or nearly all solvents when the polymers are available in the form of aqueous latex suspensions. Examples are acrylics, rubber, synthetic rubber, polyvinylidene chloride, etc. The solid or droplet core particles are suspended in the latex and the suspension fed to the rotating element according to the present invention. Moist air must be blown over the disc surface or other means provided to prevent the latex from drying and coagulating on the disc. After the coated particles and smaller excess pure latex particles leave the disc they are dried, e.g., by falling through a chamber through which hot unsaturated air or gas is passing. As water is removed from the latex, the polymer particles coagulate into an insoluble film. When dry the film coating is a tight barrier only affected by solvents for the polymer.

Figure 2:
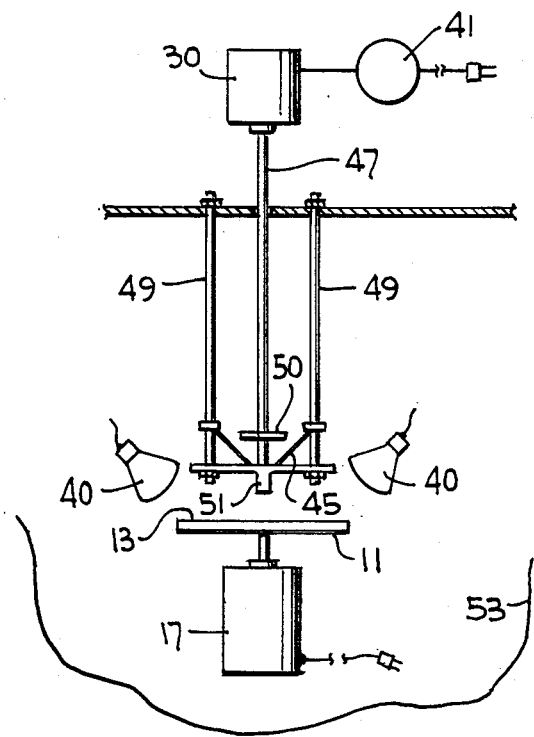
FIG. 2 is a diagrammatic illustration of an alternative embodiment of the present invention.

Another embodiment of the present invention is illustrated in FIG. 2 to which reference is now made. A rotating disc 11 with a grooved top surface 13 and its drive motor 17 are similar to like components illustrated in the embodiment of the FIG. 1. Infrared heat lamps 40 are employed to heat the space above disc 11 and a stirrer motor 30, having its speed controlled by a VARIAC 41, stirs the coating and core materials to provide the necessary suspension. A heated funnel 45 is selectively raised and lowered along three threaded vertical support rods 49, only two of the support rods being illustrated in FIG. 2. The stirrer 50 is disposed within funnel 45 and is rotated by means of drive shaft 47 connected to stirrer motor 30. The distal end of shaft 47 is in the form of a plug 51 which, depending upon the height of the funnel 45 on support rods 49, may project through the lower funnel opening and thereby close off outflow from the funnel to the disc 11. This embodiment eliminates the ball valve and provides flow control by means of the raising and lowering of the funnel on shafts 49, or by raising and lowering the motor. Many more feed schemes will be apparent to those skilled in the art.

Another embodiment of the present invention is illustrated in FIG. 3 to which detailed reference is now made. A rotating disc 55 having a smooth flat upper surface 57 is disposed horizontally between two horizontal walls 59 and 60. A funnel 61 contains a stirrer 63 placed to suspend solid particles in liquid coating material which is added simultaneously to the stirred funnel. The lower end of funnel 61 extends through a suitably provided opening 65 in upper wall 59 so that the bottom opening of funnel 61 is disposed to permit the funnel contents to fall on the disc surface 57 in alignment with the rotation axis of the disc. A distribution cone 67 diverges downwardly and is disposed substantially concentrically about the funnel stem so as to prevent splashing of the slurry material delivered from the funnel to the disc surface. Hot air is channelled to the region between plates 59 and 60, both above the disc 55 and below it, by means of suitable hot air conduits 69 which communicate with suitable openings in plates 59 and 60. The temperature of the air delivered through conduits 69 is sufficient to maintain the coating material in molten form when it is located in the region between plates 59 and 60. It is apparent that the plates aiding in controlling air flow need not be parallel. For example, higher hot air velocity at the edge of the rotating disc can be achieved with the gap between plate and rotating disc decreasing as the radius increases. It is also apparent that the plates may rotate in common with the disc.

In the Embodiment of FIG. 3, the funnel 61 serves as the vessel in which the solid particles or liquid droplets of core material are dispersed in the coating liquid. In addition, the feed rate of the resulting suspension from the funnel onto disc surface 57 is controlled by the level of suspension maintained in the funnel rather than by a funnel outlet valve mechanism.

The embodiment of FIG. 4 is similar in many respects to the embodiment of FIG. 3 except for the suspension feeding mechanism and for the fact that the disc is tilted at an angle, e.g., forty-five degrees, relative to horizontal. The suspension of coating and core materials is disposed in a vessel 70 having a stirrer 71 therein. A lower corner portion of the vessel 70 is selectively openable to permit controlled feeding of the suspension material onto the top surface 57 of disc 55. FIG. 4 is intended to illustrate that the disc can be oriented at substantially any desired angle and need not be horizontal as shown in FIGS. 1-3.

Figure 5:
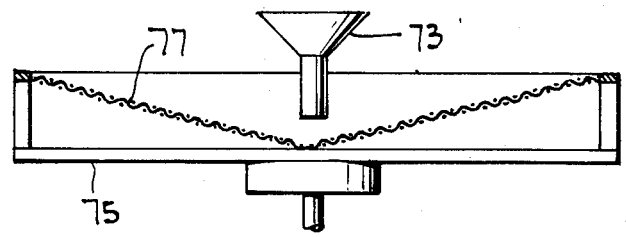
FIG. 5 is a diagrammatic illustration of yet another embodiment of the present invention.
Figure 13:
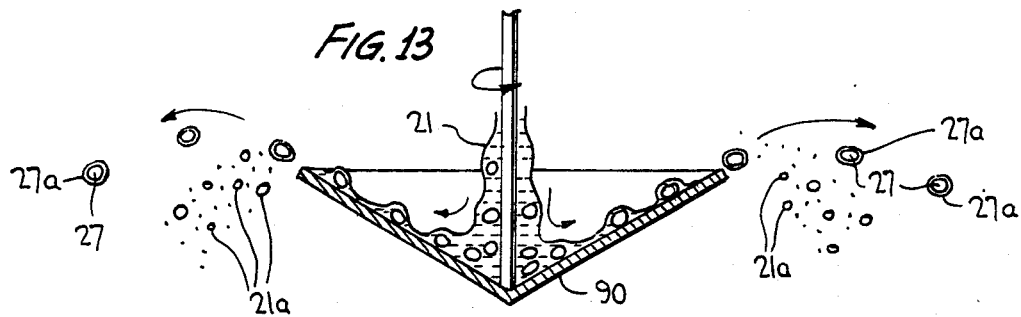
FIGS. 13 to 15 are diagrammatic views of alternative rotary separating devices useful in performance of the invention.
Figure 14:
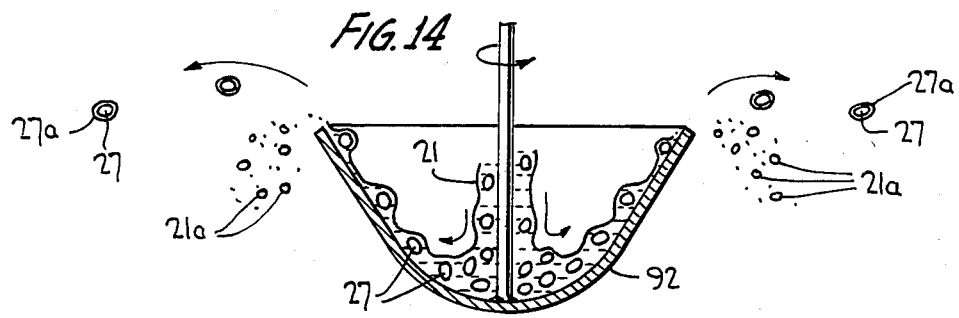
Figure 15:
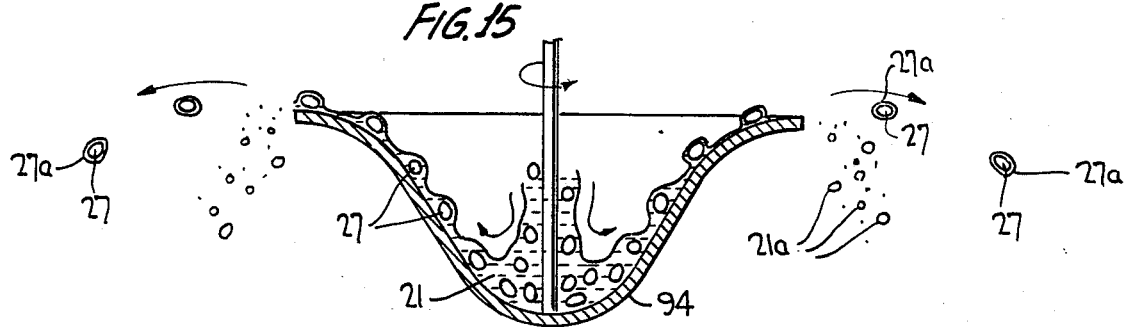

The embodiment of FIG. 5 diagrammatically illustrates the use of a generally conical mesh screen 77 disposed above the top surface of a disc 75 so as to converge to a location between the disc and the lower end of a funnel 73. The funnel delivers the suspension material toward the disc 75 in the manner described above in relation to the embodiments of FIGS. 1-3. However, the mesh screen 77, which rotates with disc 75, is provided to aid in controlling the average coating thickness by draining away part of the coating material through the screen. Further forms of rotary discs 90, 92, 94 which may be used for the invention are shown in FIGS. 13 to 15. In addition, multi-tier rotating discs, vaned wheels, grooved discs and radial tubes can be employed.

The invention as described hereinabove is suitable for coating particles of substantially any shape; however, the most uniform coating is obtained with spherical particles. Particle size may generally vary in the range from 10 micrometers to 10 millimeters, although special designs or conditions will permit the use of particles outside this range. Nearly spherical particles may be readily formed by techniques well known in the prior art, such as spray drying or prilling, by extrusion or compression in molds, or by agglomeration of fine powders in rotating drums using a liquid phase binder and/or heat. It is also known that compact crystals approaching a spherical shape may be obtained by attrition during crystallization.

The preferred coating material for minimum process cost should be liquid at coating temperature and should solidify when cooled, without requiring either evaporation of a solvent or a chemical reaction. The viscosity of the coating material may range from 0.5 to 100,000 centipoises, with preferred viscosities between 1–5,000 centipoises. Preferred coating liquids are various mixtures of polyolefins, ethylene-vinyl acetate copolymer and waxes. A typical coating liquid composition is 50 percent by weight polyethylene of density 0.92, melt index 250, and 50 percent paraffin wax having a melting point of 60° C. It is preferable that the core material is insoluble in the coating liquid at coating temperature, although soluble cores can be coated if the contact time with the coating before spraying and solidification is sufficiently short to prevent dissolution.

During a typical operation, as noted above, the particles to be coated may constitute up to 45 percent by volume of the overall suspension slurry, although in general the percent by volume will be in the 20–35% range. The temperature surrounding the top surface of the disc must be above the melting point of the coating material. Typically, this may be between 60° and 90° C. for pure waxes and 120° to 160° C. for polymer/wax mixtures.

The rotational speed of the disc is chosen so that the excess coating material produces much smaller spheres than the coated particles. If the disc were used simply as an atomizer for the coating liquid it is these small spheres which would be produced. Since the excess liquid wall material forms smaller droplets, the aerodynamic drag force per unit mass is much higher than that for the larger coated particles. Hence, as these smaller droplets solidify they are slowed down much more quickly by the drag force as they move away from the spinning disc. These droplets, therefore, fall much closer to the spinning disc. A receiver may be placed near the disc to catch these small unused coating particles for recycling back to the coating reservoir. Alternatively, the unused coating particles may be caught in the inner portion of the bottom cone for sieving and recycling.

When the ring of unused coating particles partly overlaps the ring of coated particles, the particles cannot be totally separated by sieving. When this occurs, an increase in rotational speed of the disc causes a separation of the rings, by throwing the coated particles farther and decreasing the size of the unused coating particles so that they fall closer to the disc. When the product particles are less than 100 microns in diameter, both the product and the smaller excess coating particles fall within a few feet of the disc and are both strongly affected by the air blowing outward along the radius of the disc. Hence they do not separate cleanly into distinct rings. However, they are easily separated by sieving, centrifugal force, etc.

For particles in the range of 0.5 millimeter diameter and a density of 1.2, a rotational speed of 1,000–1,500 rpm for a disc of 8-inches diameter provides good spatial separation of the fine excess wax particles from the much larger coated particles so that the excess wax particles may be collected separately and may not require a separate sieving operation.

The particles to be coated may be mixed with the melted coating material immediately before the resulting suspension is fed to the disc. Feeding rates for a disc having an 8 inch diameter are preferably on the order of 100 milliliters to 5 liters per minute but can cover the range of 10 ml/min to 100 liters/min. For coating materials with melting points substantially above room temperature (e.g., above 50° C.), the coated particles solidify rapidly after leaving the disc surface and may be collected immediately. If a solution is used as the coating, then the solvent has to be evaporated before essentially dry particles can be collected.

The embodiments described above include a disc having a grooved surface, a disc having a flat smooth surface, cupped or cone-shaped surface, and angled screens or perforated plates disposed above a reservoir (rotating or non-rotating). It is also possible to provide a vaned disc whereby the disc comprises a plurality of angularly spaced vanes with gaps therebetween. Virtually any rotating device which can be used for atomization may be used in the present application, as long as the slurry does not have to pass through a fine orifice where plugging may occur.

Other alternatives are an inverted cone made from stainless steel screen and a vaned disc in which the vanes are placed at an angle to the disc diameter.

In employing the invention, we have successfully coated the following substances: phosphors (12–60 micrometers), potassium chloride angular particles (25–300 micrometers), potassium chloride (approximately spherical particles 500–860, 250–500, 120–250 micrometers), water thickened with carboxymethyl cellulose, sucrose crystals (1–1.5 millimeters), sucrose spheres (1.4–2 millimeters), aspirin powder (held together with carboxymethyl cellulose solution), acetaminophen (180–320 micrometer spheres), etc.. Coating liquids which we have employed include pure wax, wax with solvents (e.g., paraffin wax 20 percent, Polywax 500 30 percent, 1,1,2, trichloroethane 50 percent), wax mixtures (Polywax 500 16 percent, ethylene vinylacetate copolymer (Elvax 420, 18% vinyl acetate, Du Pont de Nemours, Inc.) 24 percent and paraffin wax 60 percent; or paraffin wax 17 percent, Polywax 500 33 percent and Elvax 420 50 percent), polyethylene wax, wax and low density polyethylene (paraffin 50 percent and polyethylene 50 percent), Woods metal (50 percent Bismuth, 25 percent Lead, 12.5 percent Cadmium and 12.5 percent Tin), cellulosic polymer dissolved in a solvent, and solutions of mixtures of waxes, polyethylene and ethylene-vinyl acetate copolymer in aromatic and aliphatic hydrocarbons. Coating materials have also been used in the form of slurries containing up to 37 mass percent of suspended insoluble solids, both smaller than and greater than the average final wall thickness.

The present invention is further illustrated by the following examples:

EXAMPLE I

In this example, nearly spherical particles of potassium chloride were used, the particles being of a 20–32 mesh (500–863 micrometers) fraction obtained by sieving. The apparatus was substantially that illustrated in FIG. 1 with the top surface of disc 11 smooth rather than grooved. The outlet opening 37 for the ball valve was disposed approximately ⅛ inch above the surface 13 of the disc. The entire reservoir was heated by electrical tape and was equipped with a thermocouple. The disc was inclined at about 45 degrees from horizontal (as in the FIG. 4 embodiment) to increase the path of the upward-directed particles in the air so as to allow them to solidify before encountering a solid surface. (The downward- directed particles were not collected). The disc assembly was equipped with three heat guns above the disc and two below the disc in addition to the two heat lamps.

Thirty-eight grams of paraffin wax (Fisher P-22), 38 grams of Polywax-500 (made by the Bareco Division of Petrolite Inc.), and 24 grams of Elvax 420 (DuPont) were melted and mixed in a beaker. The molten wax and 38 grams of potassium chloride particles were mixed in the heated mixing reservoir. With all the heat guns on, the disc was then turned on to rotate at 700 rpm. The valve was opened to allow the suspension to flow onto the center of the disc from which it was dispersed. Coated potassium chloride was thrown in an upward trajectory (because of the angle of the disc with respect to horizontal) landing at floor level roughly six feet away from the disc. The smaller pure wax particles followed a path much closer to the disc, separated by one or two feet from the coated potassium chloride particles.

The large particles were separated into three fractions by sieving. Twenty-eight percent were greater than 860 micrometers in diameter; 68% were between 590 and 860 micrometers in diameter; and 4% were less than 590 micrometers in diameter. The small wax particles immediately around the disc were not recovered.

The mean diameter measured for a small number of uncoated particles (n=15) was 521±44 micrometers. The coated particles had a mean diameter of 759 plus or minus 74 micrometers (N=15). Therefore, the mean wall thickness based on these measurements was 119 micrometers.

In the fraction having a diameter greater than 860 micrometers, all the particles sank in a liquid of density approximately 10% greater than that of the wax (i.e., diethyl succinate having a density of 1.047 grams per cubic centimeter). This indicates that all these particles contained potassium chloride. In the particles having diameters in the range of 590-860 micrometers, three particles out of twenty randomly chosen particles floated, indicating that they were pure wax. (The fraction of pure wax particles in this size range could be decreased by higher disc speed or lower coating viscosity). Water extraction showed that the fraction having diameters greater than 860 micrometers contained 54.7% potassium chloride, and 45.3% wax; the fraction having 590-860 micrometer diameter contained 65% potassium chloride and 35% wax.

Whereas the free potassium chloride dissolved within seconds when placed in water, less than 3% of the coated potassium chloride (of either size fraction) dissolved in ten minutes. Only 16.2% dissolved in 70 minutes from the 590-860 micrometer fraction, and 30.9% dissolved in 70 minutes from the fraction having diameters greater than 860 micrometers. In 266 minutes, 39% dissolved from the fraction in the range of 590-860 micrometer diameter, and 62%, from the fraction having diameters in the range greater than 860 micrometers. This indicates that the soluble potassium chloride particles were well coated.

In this example (I) the potassium chloride was well coated by the waxy polymer coating. This is difficult by methods such as fluid-bed coating because the waxy droplets do not wet the potassium chloride surface well. Hence, the coating spreads poorly over the surface. In the present invention, the particles start by being totally immersed in the coating, and the process is so rapid that the coating does not have sufficient time to uncover the surface before solidifying.

EXAMPLE II

Non-pareil sugar spheres ranging from 1.2 to 2 millimeters in diameter were encapsulated in wax having the following composition: Gulfwax (household paraffin wax) 38 grams; Polywax 500 (Bareco) 38 grams; and Elvax 420 (DuPont) 24 grams. While the wax was stirred at 104° C. in the mixing vessel, 40 grams of non-pareil spheres were added, mixed well and the dispersion was poured on to the disc, which was spinning at 1140 rpm. The resulting wax coating on the coated non-pareils ranged from 17 to 25% by weight when measured by extraction. Uncoated non-pareil spheres released 73.6% of their contents in ten minutes and 91% in thirty minutes. Coated spheres did not release a detectable amount in ten minutes (i.e., less than 1%). After thirty minutes, 1.1% was released, and after one hour 2.6% was released. Hence, the sugar was well coated.

EXAMPLE III

Twenty grams of cellulose acetate butyrate (Eastman CAB 381-2) were dissolved in a mixture of 100 milliliters dichloromethane and 10 milliliters acetone and placed in reservoir 20. Red sugar crystals having a total weight of 28 grams and passing through a 500-micron sieve but retained by a 250-micron sieve were mixed with the CAB solution and the suspension fed to the disc rotating at 1170 rpm without heating. The red particles were well separated from the smaller, uncolored polymer droplets during the coating operation. The fraction of the coated product passing a 1 millimeter sieve but retained by 860 micrometer openings (coated particles agglomerated on the receiving surface due to inability to evaporate all the solvent in the laboratory air) were 68% sugar and 32% cellulose acetate butyrate coating. When placed in water, 33% of the sugar dissolved in ten minutes, and 65% in 90 minutes.

EXAMPLE IV

In order to coat with polymeric compositions of higher melt viscosity (e.g., polyethylene), it is necessary to control the air temperature adjacent to the rotating disc. This was achieved to a greater extent using the embodiments of FIGS. 3 and 4 wherein the cover plates 59 and 60 were employed. Hot air (for example, from heat guns) is conducted directly through conduits 69 toward the disc.

100 grams of polyethylene (melt index=250) was melted in a beaker. 34 grams of spherical granules of slightly water-soluble organic acid, having a number mean diameter of 0.740 millimeters, was mixed with the molten polyethylene. The temperature of the mixture was 154° C. This was delivered to the disc which was rotating at 1140 rpm. The temperature of the plates facing the disc ranged from 130° to 170° C. at different points. The viscous suspension was fed to the plate over a period of five minutes. 46 grams of material which did not contact a wall were recovered and were distributed as follows:

| Diameter (Micrometers) | % of total | Content |
|---|---|---|
| 500 | 7.8 | Polyethylene only |
| 500-590 | 0.9 | Polyethylene only |
| 590-860 | 7.3 | coated organic acid |
| 860-1000 | 14.5 | coated organic acid |
| 1000-1180 | 9.1 | coated organic acid |
| 1180 particulate | 3.7 | several spheres |
| non particulate | 56.7 | "taffy" and "spider webs", polyethylene containing no organic acid. |

(The non-particulate material is not observed at lower coating viscosity, but higher temperature could not be employed in this example to lower the viscosity owing to the thermal instability of the core particles).

For comparison, the particle size distribution of the uncoated organic acid spheres was as follows:

| Diameter (micrometers) | wt % |
|---|---|
| 500 | 0.4 |
| 500-590 | 1.2 |
| 500-860 | 79.2 |
| 860-1000 | 19.0 |
| 1000 | 0.3 |

The particles in size fraction 590 to 1000 micrometers contained 49% organic acid. When placed in deionized water 2.4% of the organic acid was released in 16 hours, 7.1% in 72 hours. In the uncoated control runs, the organic acid dissolved entirely in approximately 30 minutes.

EXAMPLE V 400 gm Woods metal, (obtained from Federated Metal Corp. of Newark, N.J.) was melted in a beaker. 50 gm of nearly spherical KCl, passing a sieve with 860 micron openings but being retained by a 500 micron sieve, was heated to 85° C. in an oven. An 8-inch disc with twenty-four grooves ⅛ inch wide and 1/16 inch deep, held at 60° C. and an inclination of 28 degrees with the horizontal, was rotated at 6,300 rpm. A suspension of KCl particles in the liquid Woods metal was formed and poured onto the disc.

The distribution of particle sizes was as follows:

| Diameter (micrometers) | Wt/(gm) | Content |
|---|---|---|
| Below 500 | 26.3 | metal dust |
| 500–590 | 21.8 | spheres |
| 500–860 | 10.0 | spheres and flat pieces |
| Above 860 | 37.1 | agglomerates |

The spheres were covered with the metal as determined by visual observation, but the potassium chloride dissolved readily, indicating that the coating was porous. Under the microscope the coating was seen to consist of many small metal crystals, giving the likelihood of leakage at crystal boundaries.

EXAMPLE VI 50 gm Polyethylene USI (density=0.927, melt index=250) was dissolved in 50 gm Gulfwax Paraffin at 150° C. The flat, smooth 8-inch diameter disc was held at 130° C. and rotated at 1,800 rpm. 50 gm of nearly spherical acetaminophen particles, 177–250 micrometers in diameter was mixed with the polymer/wax solution. The 177–300 micrometers product fraction contained mostly coated single particles.

EXAMPLE VII

The cone-screen embodiment of FIG. 5 was employed in coating nearly spherical KCl. The percent core material relative to total particle (i.e., payload) increased in the product from a run made under the same conditions using a flat disc. This demonstrates that the porous cone represents another means to control wall thickness by increasing the amount of coating liquid drained away from the core particles, and also decreases the fraction of excess coating liquid atomized from the edge of the rotating device. There is, however, a decrease in the number of discretely coated particles.

Coating composition was 38% by weight paraffin wax (Gulf), 38% by weight Polywax 500, Bareco, and 24% Elvax 420 (Dupont). Original particle size range was 0.50 to 86 mm. The slurry was fed to the disc or rotor at 116 degrees centigrade, with the air between the plates kept at 129°–133° C.

| | % Payload | |
|---|---|---|
| | 500–590 micrometers | 590–850 micrometers |
| Flat Disk | 75.8 | 57.3 |
| Cone Screen | 88 | 82.8 |

For the smooth disc, operated at the same conditions the size distributions of uncoated core particles, coated particles and atomized excess coating were as follows:

| Uncoated KCL | | |
|---|---|---|
| Diameter (micrometers) | Weight (gm) | % |
| Smaller than 420 | .418 | 2.5 |
| 420–500 | 2.354 | 14.0 |
| 500–590 | 13.187 | 78.6 |
| 590–860 | 0.654 | 3.9 |
| Larger than 860 | 0.172 | 1.0 |
| Total | 16.785 | 100.0 |

| Product (in two rings around rotating device): Coated KCL Particles (Outer Ring) | | |
|---|---|---|
| Diameter (micrometers) | Weight (gm) | % |
| Smaller than 500 | .3 | 1.8 |
| 500–590 | .6 | 3.6 |
| 590–860 | 12.1 | 73.4 |
| 860–1.00 | 2.6 | 15.8 |
| 1.00–1.18 | 0.5 | 3.0 |
| Greater than 1.18 | 0.4 | 2.4 |
| Total | 16.5 | 100.00 |

| Atomized Excess Coating (Inner Ring) | | |
|---|---|---|
| Diameter (micrometers) | Weight (gm) | % |
| Smaller than 149 | 1.0 | 5.5 |
| 149–177 | 0.9 | 5.0 |
| 177–250 | 1.5 | 8.3 |
| 250–297 | 3.3 | 18.3 |
| 297–420 | 7.3 | 40.6 |
| 420–500 | 1.3 | 7.2 |
| Greater than 500 | 2.7 | 15.1 |
| | 18.0 | 100.00 |

There is only a small overlap in the size distribution of the large coated KCL particles (mostly single coated particles) and the small droplets, which consist mostly of atomized pure coating material. Since solid KCL is more dense, nearly all coated KCL particles would be in the outer circle. If the disc is operated at higher rotational speed or if the viscosity of the coating is decreased, the diameter of the atomized droplets in the inner ring decreases. The diameter of the ring containing the large coated particles will increase if rotational speed is increased, or will decrease slightly if speed is kept the same but viscosity is decreased, because they have a thinner coating.

We have described an improved method and apparatus for coating or microencapsulating solid particles or viscous liquid droplets applicable to a wide range of sizes. The coating technique works well for coating solids in the 20–300 micrometer range where prior art methods of spraying the coating onto fluidized particles work poorly or not at all. In general the method is less expensive than prior art processes because it is very rapid and requires less energy and process control. Contact time between the coating material and the core material can be maintained extremely short. In addition, the particles need only be handled once in the apparatus as opposed to many passages through the spray region of the spray coating methods.

The present invention is also useful in place of a variety of other processes for forming microcapsules. For example, the method of the present invention obviates the need for careful control and timed changes in conditions required in many cases of coacervation and solvent evaporation microencapsulation processes. The present method avoids the difficulties of microcapsule agglomeration, a frequent problem in these processes.

The method of the present invention is also useful with dispersed liquid core droplets, made more viscous than the coating liquid to limit the spreading and atomization phenomena to the less viscous coating material. In this manner, the process of the present invention may be employed to form microcapsules similar to those formed by the annular-jet method.

Having described several embodiments of the new and improved method and apparatus for coating or microencapsulating solid particles or viscous liquid droplets in accordance with the present invention, it is believed that other modifications, variations and changes will be suggested to those skilled in the art in view of the foregoing description. It is therefore to be understood that all such variations, modifications and changes are believed to fall within the scope of the invention as defined in the appended claims.

What is claimed is:

1. A method of coating or encapsulating individual mass components of core material having the form of solid particles, aggregates formed by granulation or liquid droplets with a coating of material that is less viscous than the core material and solid at normal room temperatures but liquid at elevated coating temperatures, or in the form of a solution during the coating process, said method comprising the steps of:

distributing said individual mass components of core material throughout the liquid coating material to form a suspension;

feeding the suspension onto a rotating surface which centrifugally separates and disperses the suspension into (1) droplets of pure coating material and (2) individual components of said core material coated with said coating material;

cooling the coated individual mass components or removing solvent therefrom to solidify the coating material;

and controlling the process so as to produce a predominance of the droplets of excess liquid coating as droplets of a predetermined size smaller than the size of the coated individual mass components.

2. The method according to claim 1 further comprising the step of separating said coated individual mass components from the droplets of pure coating material by rotating said rotating surface at sufficiently high speed such that the droplets of pure coating material are significantly smaller than the coated individual mass components and therefore fall from said rotating surface at a location radially inward from the separated coated individual mass components.

3. The method according to claim 1 further comprising the step of heating the region at said rotating surface to maintain the coating material in liquid form at said rotating surface.

4. The method according to claim 1 wherein the step of distributing comprises the steps of:

heating said coated material in a vessel to sufficiently high temperature to maintain the coating material in liquid form;

dispersing said individual mass components of material into said coating material in said vessel; and stirring the contents of said vessel to form said suspension of individual mass components distributed throughout said coating material.

5. The method according to claim 1 wherein the rotating surface is oriented at an acute angle relative to horizontal.

6. The method according to claim 1 further comprising the step of adjusting the thickness of the coating material on said core material by (a) adjusting the rotational speed of said surface, (b) adjusting the viscosity of the liquid coating; (c) adjusting the rate at which said suspension is fed onto said rotating surface in said step of feeding; or (d) altering the wetted surface area of the rotating device.

7. The method according to claim 1 further comprising the steps of:

draining a portion of said coating material, which is fed as part of said suspension to said rotating surface, by providing porosity in said rotating surface as with a mesh cover or porous material or perforated material disposed in the form of a cone or bowl in spaced relation above a further receiving surface;

centrifugally dispersing the coated mass components, which are larger than the interstices or perforations of said mesh cover, along said mesh cover while partially draining the liquid coating material, by gravity, suction and/or centrifugal force, away from the coated mass components as the mass components move along the mesh cover; and passing said liquid coating through the mesh cover and recycling the passed liquid coating material.

8. The method according to claim 1 further comprising the steps of:

solidifying said droplets of coating material; and recycling the solidified droplets of coating material by returning them to said suspension.

9. The method according to claim 1 further comprising the step of adding a solvent for said coating material to dissolve the coating material prior to or during the formation of the suspension to permit coating or to reduce the thickness of the coating material on said coated mass components.

10. The method according to claim 1 wherein said core material is at least partially soluble in said coating material, and wherein the time from initial contact between said core and coating materials to solidifying of said coating material is sufficiently short to prevent significant dissolution of said core material into said coating material.

11. The method according to claim 1 wherein the core material or a component contained thereon reacts with the coating material or a component contained therein to form an initial solid wall at the periphery of each individual mass component before said coating material solidifies.

12. The method according to claim 1 wherein said core material is in the form of liquid droplets having a higher viscosity than that of the coating material.

13. The method according to claim 12 wherein said individual mass components are generally spherical particles having diameters in the range of 10 micrometers to 10 millimeters.

14. The method according to claim 1 further comprising the step of hardening the coated mass components by transferring them to a chemical hardening bath.

15. The method according to claim 14 wherein said coating material comprises gelatin and (a) said hardening bath includes glutaraldehyde; or hot gas, air or non-solvent liquid is contacted with the gelatin to cause cross-linking and insolubilization or hardening.

16. The method of claim 1 wherein the coating liquid is a suspension containing fine insoluble particles which become part of the coating on the core particles, and are equally as well distributed in the excess coating liquid.

17. The method according to claim 1 wherein said suspension is flung radially outward along said disc surface in radially-extending angularly-spaced channels formed in said surface.

18. In a process for coating particles with a liquid coating, a method for obtaining individually coated particles while simultaneously facilitating removal of the coated particles from excess coating liquid with which the particles are mixed in a suspension, the method comprising feeding the suspension to a rotating surface to separate the suspension into coated particles and atomized liquid droplets expelled circumferentially from the surface, and rotating the surface at a speed for obtaining a predominance of the excess pure coating droplets of a predetermined size which is smaller than the size of the coated particles.

19. The invention of claim 18 wherein the volume percentage of particles to be coated in the suspension is in the range 10-35%.

20. The invention of claim 18 wherein the core mass components to be coated are poorly wetted by the coating liquid (wetting angle less than 90°) but are completely coated by virtue of having been completely immersed while in suspension and having the process of liquid spreading and particle radial passage and solidification occur too rapidly for the uncovering of the core to occur.

* * * * *